United States Patent
Knuth et al.

[11] Patent Number: 5,865,842
[45] Date of Patent: Feb. 2, 1999

[54] SYSTEM AND METHOD FOR ANCHORING BRAIN STIMULATION LEAD OR CATHETER

[75] Inventors: Henricus M. Knuth, Kerkrade; Johannes F.M. Gijsbers, Mustergeleen, both of Netherlands

[73] Assignee: Medtronic, Inc., Minneapolis, Minn.

[21] Appl. No.: 705,566

[22] Filed: Aug. 29, 1996

[51] Int. Cl.$^6$ .................................................. A61N 1/05
[52] U.S. Cl. ............................................................ 607/116
[58] Field of Search ............................ 604/175; 607/116, 607/139, 115, 149

[56] References Cited

U.S. PATENT DOCUMENTS

| | | |
|---|---|---|
| 3,663,965 | 5/1972 | Lee, Jr. et al. . |
| 3,995,644 | 12/1976 | Parsons . |
| 4,004,298 | 1/1977 | Freed . |
| 4,245,645 | 1/1981 | Arseneault et al. . |
| 4,328,813 | 5/1982 | Ray . |
| 4,474,569 | 10/1984 | Newkirk . |
| 4,578,063 | 3/1986 | Inman et al. . |
| 4,850,359 | 7/1989 | Putz . |
| 5,464,446 | 11/1995 | Dreessen et al. . |

FOREIGN PATENT DOCUMENTS 0367354  2/1993  European Pat. Off. .

OTHER PUBLICATIONS 01.05.87–JP–1062999(09.11.88) "New skin through terminal–contg.face(s) exposed to exterior through holes penetrating . . . " by Asahi Glass KK–1988 Derwent Publications Ltd.
22.12.87–JP 3222712 (28.06.89) "Terminal for through the skin use has exposed . . . " C89–102087–by Asahi Glass KK–1989 Derwent Publications.

*Primary Examiner*—Scott M. Gelzow
*Attorney, Agent, or Firm*—Michael J. Jaro; Harold Patton

[57] ABSTRACT

A connector system and method for anchoring a tubular lead or catheter member within a cranial burr hole in a patient, providing for direct in-line positioning and reliable fixation of the member with respect to the patient's skull after the distal end portion has been accurately positioned within the patient's brain. The system includes a baseplate, with or without adaptor to adapt for the burr hole size, and a two element fixation subassembly positioned within the baseplate for enabling fixing of the member to the baseplate after the member has been accurately positioned with a stereotactic instrument. The fixation subassembly suitably includes a compression seal made of a compressible material and a compression screw which, when screwed down into the baseplate, exerts an inwardly radial force on the compression seal, causing the seal to fixedly engage the lead or catheter member within the axial lumen of the baseplate. This fixation subassembly and method enable reliable anchoring of the member without any axial displacement of the distal portion. Following the compression fixation, the member is connected, preferably at right angles, and routed to a suitable electrical stimulator or fluid source.

30 Claims, 4 Drawing Sheets

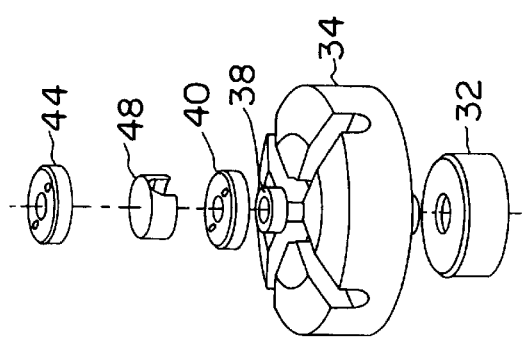
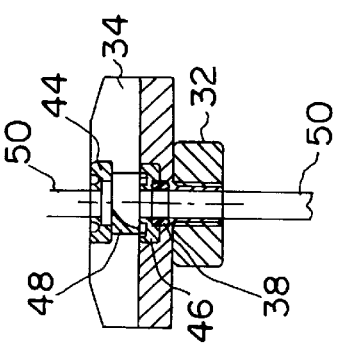
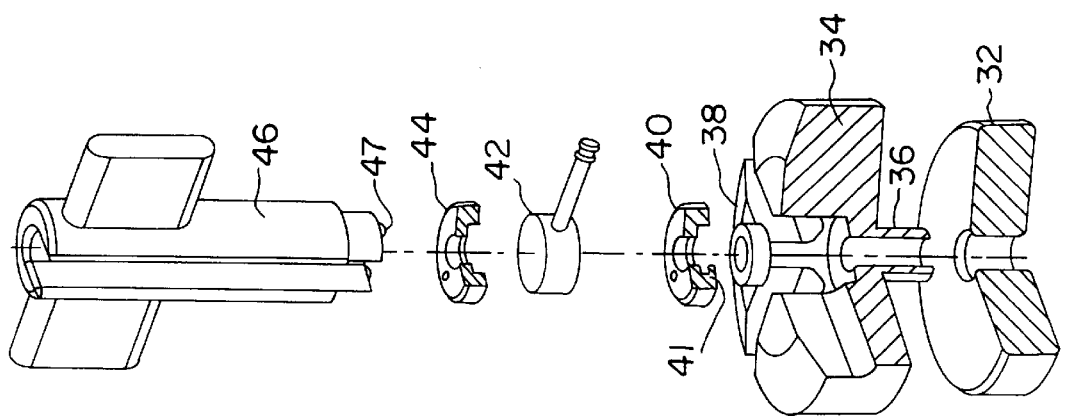
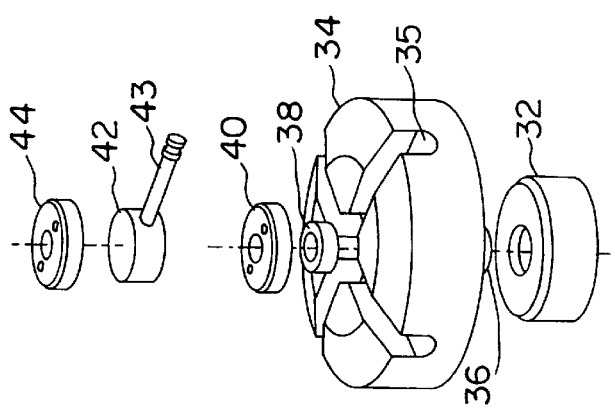
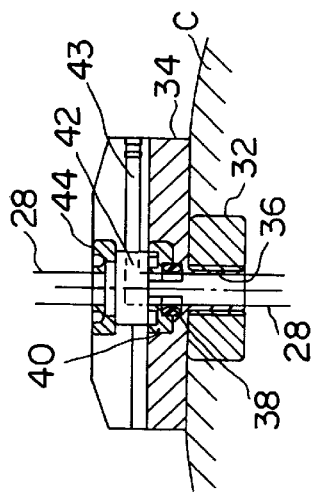

SYSTEM AND METHOD FOR ANCHORING BRAIN STIMULATION LEAD OR CATHETER

FIELD OF THE INVENTION

This invention relates to a cranial connector or anchoring system and, more particularly, to a system and method for anchoring a brain stimulation lead or cranial catheter which has been implanted through a cranial burr hole and in a selected target area of a patient's brain.

BACKGROUND OF THE INVENTION

Systems for providing either electrical stimulation of the brain or coupling fluid to or from the brain are coming into increased use for various purposes. Electrical stimulation of the brain is utilized for relief of chronic pain and treatment of movement disorders. A typical electrical brain stimulation system comprises a pulse generator operatively connected to the brain by a lead. The lead has one or more electrodes at its distal end, designed to be implanted within the patient's brain at a precise location, so that the electrode or electrodes are optimally and safely positioned for the desired stimulation. The lead is connected to the pulse generator at its proximal end, and also needs to be anchored with respect to a burr hole drilled in the patient's skull or cranium, in order to hold the distal end which carries the electrodes reliably secure. Likewise, in the case of a catheter for providing fluid to the brain or for providing drainage, it is necessary to be able to secure the distal portion of the catheter that passes through the skull and transfers the fluid at a predetermined exact location within the brain. Still further, for a combined catheter and lead member, such secure and reliable anchoring of the member so that the distal end is precisely located within the skull, is very important.

Reference is made to U.S. Pat. No. 5,464,446, "Brain Lead Anchoring System," assigned to Medtronic, Inc., which is incorporated herein by reference. The referenced patent illustrates an effective lead anchoring system, and it discusses the method of providing access through the skull by drilling a burr hole with a cranial drill, inserting a stimulation lead through the burr hole and positioning it so that the electrode or electrodes are at the desired stimulation site. The lead is positioned using a stereotactic instrument, which permits a very precise movement within the brain. Once the lead is positioned and tested to determine that the results of stimulation are satisfactory, it is critical that the lead is not to be moved, since even the slightest displacement can result in less than optimal results, and even injury to the brain.

The referenced anchoring system shows a basic anchor for fixing the lead in place with the distal portion extended through the cranial burr hole, and then securing it by bending it into a slit such that it is held by a friction fit. However, neither this system, nor any other known system, provides a reliable way for accurately securing the lead, or catheter, before it is bent into the fixation position. Thus, such systems do not provide against small movement of the distal end of the lead at the time of fixating, or securing the lead in place. What is required, and what has remained a substantial need in the art, is a system and method for accurately placing a cranial lead directly through the skull "in line," and without kinking, and which enables securing of the lead or catheter precisely in position relative to the brain before it is removed from the stereotactic instrument and connected either to a stimulator or fluid source. The cranial connector of this invention accomplishes this, and provides a sealed feedthrough for electrical or fluid connection from outside the skull to an area within the skull.

SUMMARY OF THE INVENTION

It is an object of this invention to provide a system and method for anchoring a brain stimulation lead or catheter, either one of which is hereinafter referred to as a "member", so that the distal end of the member can be securely fixed in position beneath a hole in the patient's cranium at precisely the desired location. More specifically, the object is to enable such secure fixation before release of the member from the stereotactic instrument used to position the member, and before final securing of the member so as to interconnect with a therapeutic device.

In accordance with the above object, there is provided a system for anchoring a cranial member in the form of a brain stimulation lead or fluid catheter so that the distal end of the member can be accurately positioned and held in place while the member is disconnected from a stereotactic instrument and securely positioned for connection to a pulse generator, fluid source or any other type of therapeutic device. The system has a baseplate with an upper portion which rests on and is screwed into the skull, and a lower portion which is positioned through a cranial hole that has been drilled to receive it. An adaptor ring can be secured to the baseplate lower portion in the situation where a larger hole needs to be drilled, either due to problems with the initial hole or simply due to the preference of the physician. The baseplate has an axial lumen extending therethrough configured to receive the member, and a receiving cavity in the upper portion. A fixation subassembly, preferably in the form of a compressible seal with a central lumen therethrough which is configured for snugly receiving the member, and a compression screw for holding the seal under compression, is positioned within the receiving cavity and tightened to anchor or lock the member with a radial compressive force on a portion of the member that is within the baseplate lumen. With this system and method, the member can be accurately positioned and, while it is still maintained in line by the stereotactic instrument with which it is positioned, it is secured with respect to the patient's skull.

In a preferred embodiment, the baseplate has an upper cylindrical portion with an axial lumen therethrough, and a lower extending central flange with a axial lumen therethrough. The baseplate, with or without an adaptor, is fitted into the burr hole in the patient's skull. The baseplate has at least one path, and preferably four roughly orthogonal paths extending radially from the upper lumen to the outside of the upper cylindrical portion. A connector element, for connecting either a stimulating lead or a fluid-carrying catheter, is positioned within the upper portion for making a connection from the member through a selected one of the radial grooves. The fixation sub-assembly includes a compression seal which is positioned on top of the baseplate, and a compression screw which is positioned on top of the compression seal, before the connector is installed. The compression screw is threadedly screwed into the baseplate to compress the seal, thereby securing the seal to the in-line member and thus securing the member to the baseplate and the skull. After the in-line member has been precisely secured without movement, the connector is then severed above the compression screw cap, and the member is connected through the connector either to a pulse generator or to a fluid source or drain device.

BRIEF DESCRIPTION OF THE DRAWINGS

FIG. 2A is an exploded perspective view showing the component parts of a fluid catheter anchoring system embodiment of this invention; FIG. 2B is a cross-sectional view of the system embodiment of FIG. 2A with the parts joined together.

FIG. 3 is an exploded perspective view, with some of the elements shown in cross-section, of the system illustrated in FIGS. 2A and 2B, and including a tool used in assembling the system.

FIG. 4A is an exploded perspective view of the component parts of a lead anchoring system embodiment; FIG. 4B is a cross-sectional view of the assembled system illustrated in FIG. 4A.

DESCRIPTION OF THE PREFERRED EMBODIMENTS

Figure 1:
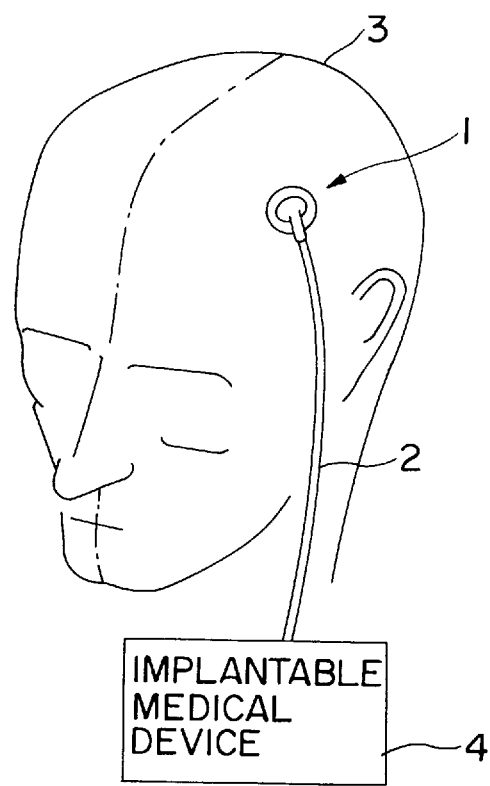
FIG. 1 is a perspective view showing an anchoring or fixation system in accordance with the invention which provides anchoring or fixation of a medical electrical lead or catheter to a patient's skull, the lead or catheter coupled at it distal end to a patient's brain and coupled at its proximal end to an implantable medical device.

Referring now to FIGS. 1A, 1B and 2, there is shown an anchoring or fixation system 1 in accordance with this invention which provides anchoring or fixation of a medical electrical lead or catheter 2 to a patient's skull 3. Typically such a lead or catheter is coupled at it distal end to a patient's brain and coupled at its proximal end to an medical device 4 or the like. In this embodiment the medical device 4 is implantable, although any suitable medical device may be used, including implantable as well as external pulse generators, drug administration system, draining systems or any other such device which emits a desired medical therapy.

Turning now to FIGS. 2 through 7, FIG. 2 shows several views of the anchoring or fixation system 1 in accordance with this invention. Installation of the anchoring system is preceded by drilling of a suitable hole in the patient's skull. Preferably the hole size is selected as the baseplate screw size, which is a standard. However, if a larger hole size is preferred by the physician, an adaptor ring is used. The adaptor ring is mounted to the baseplate prior to mounting the baseplate on the patient's head, to avoid the difficulty of handling such a small item later during the surgery. Various ring sizes are available for adapting to the hole size to be used.

Baseplate 34, either alone or, as shown connected to screw adapter 32, is positioned within a burr hole within the patient's cranium, the cranium being illustrated as C. The baseplate is screwed into the patient's skull. Adapter 32 is typically one of two different sizes, corresponding to the diameter of the burr hole that has been drilled. The adapter has an axial, or central lumen therethrough, the wall of the lumen being threaded to receive the lower flange portion 36 of baseplate 34. Baseplate 34 has an upper portion with a diameter greater than the diameter of the screw adapter, and a lower axially extending flange portion 36 which is threaded so as to fixedly engage the screw adapter 32 that has been placed within the burr hole. As is seen also in FIG. 2, baseplate 34 has an upper axial lumen with a diameter greater than the lumen portion of flange 36. Baseplate 34 also has a plurality of radially extending slots, or paths 35, adapted to fit a radial extension, or arm 43 of connector 42, as discussed hereinbelow. A compression seal 38 likewise has an axial lumen to accommodate the lead or catheter member 28. Seal 38 is suitably made of silicone rubber and has an inner diameter adapted to just receive the outer diameter of the lead or catheter member. Seal 38 is compressible, so that when compressive force is applied from top and bottom, i.e., axially, it is expands radially, providing a tight compressive fixation with the member 28. Compression screw cap 40, which also has an inner lumen to accommodate member 28, is placed down over top of seal 38, and is threaded to engage threads on the upper lumen of baseplate 34. As seen particularly in FIG. 2, compression screw cap 40 has a notch 41 to restrain seal 38 from being squeezed radially outwardly, such that the axial compression causes seal 38 to extend plastically inwardly and provide a tight fixation with the member 28. Compression screw 40 is screwed into place by tool 46, which has engaging spokes 47 which seat into complementary holes shown in screw 40.

A 90 degree fluid connector element 42, having a radially extending arm 43, is placed on top of compression screw 40, with arm 43 being positioned in a selected one of the radial slots, or paths 35. Connector 42 has a central axial opening in the bottom for communicating with the lumen of baseplate 34, which opening connects through arm 43 to provide a right angle path for fluid. In practice, another catheter-like tube is connected to the outer end of arm 43, to provide fluid transport to or from the anchoring assembly and member 28. An end cap 44, threaded on its outer circumference, is then screwed into the upper lumen of baseplate 34 with tool 46, to tightly secure the entire assembly.

Still referring to FIGS. 2A, 2B and 3, it can be now seen how the fixation assembly is utilized for direct in-line and accurate positioning of the member 28, without movement of the member at the time that it is secured in place. The member is threaded through elements 32, 34, 38 and 40, which are loosely pre-mounted, and secured to a stereotactic instrument (not shown), the use of which instrument is well known in the art. Upon accurate positioning of the distal end of the catheter or lead, and verification of such positioning, the member is held in a fixed in-line, or axial position by the stereotactic instrument. Note that at this point, there has been solely direct vertical, or in-line positioning of the member, such that at no time need it be bent at any point, which is very important in order to maintain it in a kink-free condition. The outer bottom portion of baseplate 34 rests on the top of the cranium C, as illustrated in FIG. 2B. Compression seal 38 is placed into position, and then compression screw 40 is placed down on top of seal 38, and screwed into position with the wrench, or tool 46. Note that wrench 46 is longitudinally slit, so that it can be placed around the member 28. At this time, with a proximal portion of a catheter still being secured to the stereotactic instrument, the member is now securely fixed into position within baseplate 34, due to the radially inward compressive force of seal 38. The stereotactic instrument is then released from the catheter, and the catheter is severed or cut just a short distance above where it is extends upward from the upper surface of compression screw 40. The distance that the cut catheter protrudes above the surface of screw 40 corresponds to the height of the axial portion of connector 42, to ensure that when connector 42 is next placed down on top of the surface of screw 40, the catheter makes good fluid connection into the axial body portion of connector 42. The arm 43 of connector 42 is positioned within a selected one of the slots 35 of baseplate 34. End cap 44 is then screwed into place on top of connector 42 with tool 46, resulting in the fully assembled anchoring system as shown in FIG. 2B. An external catheter, not shown, can then be connected to the tip or distal end of arm 43, to provide fluid communication between the brain and an external fluid source or sink.

Referring now to FIGS. 4A and 5B, there are shown respectively an exploded view and a cross sectional view of the same anchor assembly as shown in FIGS. 2A and 2B, with the exception of the connector element. In this embodiment, the connector is adapted to provide for a stimulus lead for transmitting stimulus pulses to the brain, as opposed to a fluid carrying catheter tube. Instead of fluid connector 42 as illustrated in FIGS. 2A and 2B, there is provided a lead guide element 48, shown in perspective in FIG. 4A and in cross-section in FIG. 4B. Element 48 is a basically cylindrical element which has a bottom opening which communicates with the lumen of compression screw 40, and which provides a 90 degree angle having an output directed radially. Lead guide element 48 has its radial opening positioned to lead directly to a selected one of the slots 35, so that the lead can be guided through element 48 and passed through the path 35 roughly parallel to the patient's skull. In application, the lead 50 is accurately positioned within the patient's brain, and tests are performed to verify the position. At this point, the lead 50 remains fixed to the stereotactic instrument which holds it firmly and reliably in the exact chosen position, as illustrated in FIG. 4B. Elements 32, 34, 38 and 40, the same as described with respect to FIGS. 2A and 2B, and having coincident axial lumens through which the lead has already been positioned, are then put into place and secured as described above. The lead now being secured by compression seal 38 and the downward force of compression screw 40, the lead is released from the stereotactic instrument. Following this, the lead is passed through lead guide 48 and the guide is positioned in place, with its opening communicating directly with a selected groove 35. End cap 44 is then secured to hold the entire assembly firmly fixed. The portion of the lead external to the anchoring assembly can then can be manipulated as desired, e.g., connected to an extender or extension lead in a known fashion.

Figure 5:
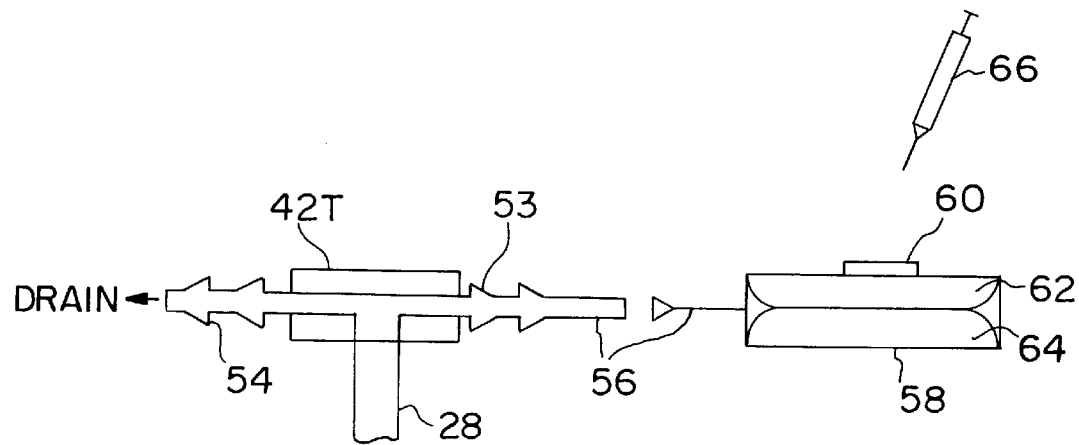
FIG. 5 is a block diagram of a fluid delivery system utilizing the anchoring system of this invention.

Referring now to FIG. 5, there is shown a schematic diagram illustrative of a fluid system having a connector 42T with a "T" pathway for providing either fluid drain or fluid delivery. Connector 42T has, on the left, an outlet 54 with connector elements for connecting a drainage tube thereto. Coming out the right as seen in FIG. 5, there is a fluid delivery pathway terminating in connector elements 53. A catheter 56 is shown connected to fluid delivery arm 53, the other end of the catheter being connected to a supply source 58. Supply 58 has a puncturable resealable membrane 60, which communicates with a reservoir 62 for holding a drug or other desired medicament in fluid form. A pump and battery are illustrated together at 64. The reservoir 62 can be filled by a syringe 66, in a known manner.

Figure 6:
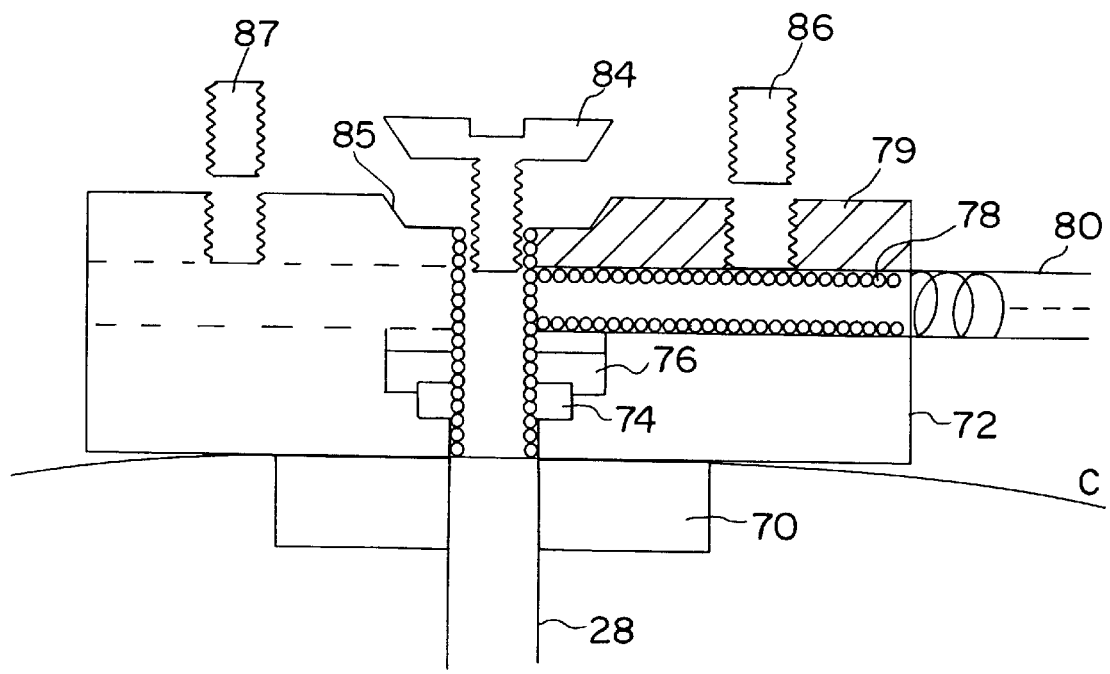
FIG. 6 is a cross-sectional view of another embodiment of a stimulation lead anchoring system with an extender connected within the anchoring system.

Referring now to FIG. 6, there is shown a diagram of an alternate embodiment of the fixation or anchor system of this invention for fixing a stimulation lead in place. In this embodiment, screw adapter 70 corresponds to prior screw adapter 32, and baseplate 72 corresponds to baseplate 34. Baseplate 72 has an upper lumen which accommodates compression seal 74 and compression screw cap 76, which are screwed into position to hold lead 28 when it has been accurately positioned. After this, and after disengagement of lead 28 from the stereotactic instrument, the lead is severed, or cut just a short distance above where it extends from the upper surface of compression screw cap 76. Reference is made to the illustrated coil conductor shown extending above screw cap 76. A contact screw 84 is screwed into a receiving opening 85, the lower length of the screw having a diameter so as to make firm contact with the coil loops at the cut end of lead 28. The screw, which is metallic, is in firm contact with an upper metallic portion 79 of baseplate 32. An external lead, or extender lead, illustrated at 80, is positioned at radial path 78, and securely fixed by set screws 86, 87, which make contact with the conducting coil 78 of lead 80. In this manner, a secure mechanical and electrical connection is made from the coil conductor of lead 28 to the extender coil portion 78. This embodiment has the advantages of avoiding extensive subcutaneous protrusions, and avoiding additional surgery as normally needed to hide the lead to lead extender interface connection. Tunneling for a subcutaneous lead extension can be done in the normal manner, taking the lead extension out just at the point where it is connected into the connector. Notice also that this arrangement allows easy lead replacement, by simply disengaging extender 80 and undoing the fixation system, so as to provide for replacement and positioning of a new lead if desired.

There have thus been illustrated several system embodiments for providing easy, efficient and in-line placement of a brain stimulator lead or brain catheter, and particularly providing for chronic fixation of the lead or catheter member while it is still being held in place by the stereotactic instrument. After accurate placement of the member within the brain, the member is reliably secured to the fixation assembly, while still being held in position by the stereotactic instrument. The feat of fixation without movement is accomplished by the combination of a compression seal and compression screw cap, which provides a radially inward compressive force on the member which is being maintained "in-line," thereby essentially eliminating any movement of the member due to bending or other tensions during fixation. Note also that the apparatus and method of the invention, in providing that the member is maintained vertical and axially in line up until it is secured in place, ensures that the installation is kink-free. In the fluid delivery or drain embodiment, a 90 degree pathway is provided by a fluid connector element, meaning that the catheter itself is never bent at 90 degrees.

Figure 7:
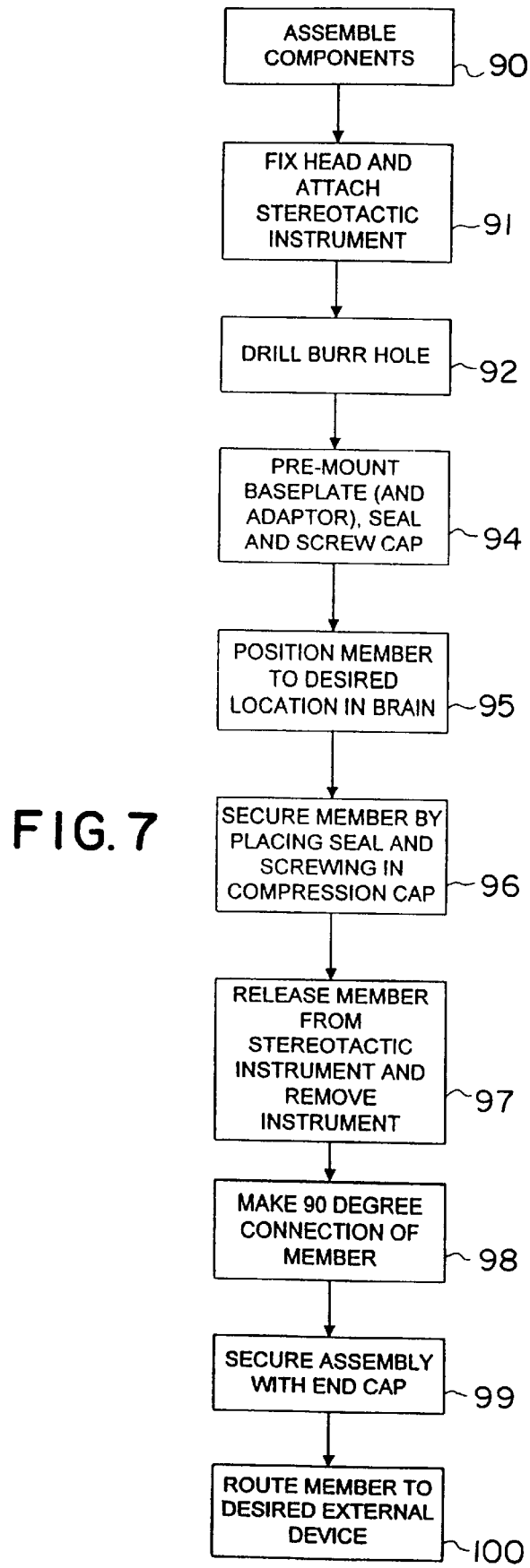
FIG. 7 is a flow diagram of steps taken in carrying out the method of this invention whereby a stimulation lead or fluid catheter is anchored in place with respect to a patient's skull.

Referring now to FIG. 7, there is illustrated a flow diagram of the steps taken in securing a lead/catheter member with the system of this invention. As illustrated at 90, the components of the system and any other supporting apparatus are assembled. This means assembling all of the constituent parts of the anchoring assembly for the chosen embodiment, the bifunctional tool, the catheter or lead to be employed, the stereotactic instrument, and any necessary test equipment. As shown at 91, the patient's head is fixed, and the stereotactic instrument, or frame is mounted on the head. Following this, the burr hole is drilled through the patient's skull, as indicated at 92. If the physician selects a hole size greater than the standard size, an appropriate adaptor is selected.

With everything in place, at 94 the physician premounts the baseplate (including adaptor, if necessary), seal 38 and compression screw cap 40. Following this, the catheter or lead member is positioned, using the stereotactic instrument, to the desired location in the brain, as indicated at 95. Following this, and while the lead is held secure by the stereotactic instrument, at 96 the member is secured to the skull by placing the compression seal in the baseplate and screwing on the compression screw cap, thus causing radial compression against the outer wall of the member and holding it in fixed position with respect to the baseplate, and thus the patient's skull. Following this, the catheter or lead member is released from the stereotactic instrument, and the instrument is in turn removed from the patient, as shown at 97. A 90 degree connection of the member is then made, as illustrated at 98. For a first fluid catheter embodiment, this means severing the catheter just above the compression screw upper surface, and then placing a 90 degree fluid connector element in place. For a first lead embodiment, this step involves threading the lead through a 90 degree lead guide, and positioning the lead guide in place on top of the compression screw surface. Following this, as illustrated at 99, the assembly is secured by screwing in an end cap to the top of the baseplate. The procedure is completed by routing the member, either fluid catheter or electrical stimulation lead, to a desired extender member and thence to an external device, e.g., a fluid pump or a stimulus generator, as shown at 100. Alternately, for the anchoring embodiment of FIG. 5, a 90 degree connection for a stimulation lead is made by inserting an extender conductor laterally through a path in the baseplate to make electrical contact with the conductor of the stimulus lead, following which electrical and mechanical connection of the lead conductor and extender conductor is secured as described above.

There has thus been disclosed a connector system and method of accurately and reliably connecting a cranial catheter or lead member, whereby the distal end of the member is reliably positioned at a chosen location within the patient's brain. The connection system of this invention provides an effective feedthrough connector for either electrical transmission, as through a brain stimulation lead, or fluid connection as through a brain catheter. The connector system and method of anchoring same enable straight in-line positioning of the member, and particularly enable accurately securing the member without movement after the member has been positioned to the optimal location. It should be understood that the present invention is not limited to use only in anchoring electrical leads, but may be used in many of various types of therapeutic or diagnostic devices, including muscle, nerve or defibrillation leads. It is to be further understood, moreover, the present invention may be employed in many of various other types of therapeutic or diagnostic catheters. For purposes of illustration only, however, the present invention has been described in the context of electrical leads and catheters. As used herein, however, the term lead is used in its broadest sense and includes any other elongated member, including a catheter, which may be usefully introduced into the body.

What is claimed is:

1. A system for anchoring a tubular lead-type member within a cranial burr hole in a patient, comprising:
    a baseplate, the baseplate having an upper cylindrical portion with an upper axial lumen therethrough and a lower extending central flange with a lower axial lumen therethrough, the upper and lower lumens being configured to receive the member, and the baseplate flange being positioned within the burr hole;
    fixation means positioned within the upper baseplate portion for fixing the member to the baseplate, the fixation means having a lumen therethrough for receiving the member; and
    connector means positioned above the fixation means and within the upper portion for making a connection to the member,
    whereby the member can be inserted axially through the fixation means lumen and through the upper and lower baseplate lumens, fixed to the baseplate, and then connected to the connector.

2. The system as described in claim 1, wherein the tubular member is a brain lead for conducting electrical signals, and further comprising an external lead connected to the brain lead at the connector means.

3. The system as described in claim 1, wherein the baseplate comprises an adaptor adapting the baseplate to the burr hole.

4. The system as described in claim 1, wherein the tubular member is a brain catheter for carrying fluids to or from the patient's brain, and further comprising an external catheter connected to the brain catheter at the connector means.

5. The system as described in claim 4, wherein the baseplate comprises at least one radial path, and the connector means comprises a 90 degree fluid connector having an axial portion positioned within the upper axial lumen and a radial portion positioned within the path.

6. The system as described in claim 5, wherein the fixation means comprises a compression seal positioned below the connector means and within the upper lumen.

7. The system as described in claim 5, wherein the fixation means comprises a screw cap with a first axial lumen therethrough positioned distal to the connector means, and a compression seal with a second axial lumen therethrough positioned proximal to the connector means.

8. A system for anchoring a brain stimulation lead so that the distal end of the lead is securely fixed in position beneath a hole in a patient's cranium, comprising:
    baseplate means for fitting into and securing to the hole, the baseplate means having an axial lumen extending therethrough configured to receive the lead, and an upper portion having a receiving cavity, and
    fixation means positioned within the receiving cavity for fixing the lead to the baseplate means, the fixation means comprising a compressible seal having a central lumen aligned with the axial lumen and configured for snugly receiving the lead therethrough, and compressing means for holding the seal under compression, whereby the seal central lumen is compressed to fixedly engage the lead.

9. The system as described in claim 8, wherein the baseplate means comprises at least one slot extending radially from the axial lumen, and further comprising connection means for providing a 90 degree path from the axial lumen into the slot, whereby after the lead has been fixed by the fixation means it can be positioned through the slot so as to exit the baseplate at about 90 degrees relative to the baseplate lumen.

10. The system as described in claim 8, wherein the compression seal is made of silicone rubber.

11. The system as described in claim 8, further comprising right angle guide means for guiding the lead at a right angle to the axial lumen, and securing means for securing the guide means to the baseplate means.

12. The system as described in claim 8, wherein the lead is terminated just above the fixation means, and comprising connector means for electrically and mechanically connecting an extender lead to the lead just above the fixation means.

13. The system as described in claim 12, wherein the baseplate means upper portion has a pathway for receiving the connector means.

14. The system as described in claim 8, wherein the compression means has outward restraining means for restraining radially outward extension of the compressible seal, whereby when the seal is compressed it extends radially inward and engages the member.

15. A method for in-line placement of a brain member selected either from a stimulus lead or a fluid delivery catheter, the method comprising:

in-line positioning the member so that a distal end thereof is in a desired position within the patient's brain, and a proximal portion thereof extends outside of the patient's skull;

securing the member just above the patient's skull with radially inward compressive force on the member, and after the securing, making an operative connection from the secured member to an external element.

16. The method of claim 15, comprising selecting a stimulus lead, and making a 90 degree connection to the lead just above the point where the lead is radially secured.

17. The method of claim 15, comprising selecting the member to be a stimulus lead, and further comprising cutting the lead to leave a proximal portion just above the point where it is radially secured and making an electrical connection from the proximal portion to an extender lead.

18. The method of claim 15, comprising selecting the member to be a fluid catheter, and further comprising cutting the catheter just above the point where it is radially secured, and connecting an external catheter to the cut catheter.

19. A system for anchoring a brain stimulation or fluid catheter member within a cranial burr hole in a patient, comprising:

baseplate means securable to the patient's skull for providing a central lumen through the burr hole, the baseplate means having a receiving area;

compression means positioned in the receiving area and having a central lumen therethrough for providing a radial compression force against the member when it is positioned through the baseplate lumen and the compression means lumen.

20. The system as described in claim 19, wherein the compression means comprises a compressible seal and a compression screw, the screw being configured to cause inward radial expansion of the seal when it is screwed toward the seal.

21. A brain stimulation system comprising:

an electrical pulse generator;

a lead having a proximal end and a distal end, the proximal end having a connector to connect the lead to the electrical pulse generator, the distal end having at least one electrode to connect the lead to the brain;

means for anchoring the lead to a skull of a patient, the means for anchoring having baseplate means for fitting into and securing to the skull, the baseplate means having an axial lumen extending therethrough configured to receive the lead, and an upper portion having a receiving cavity, and fixation means positioned within the receiving cavity for fixing the lead to the baseplate means, the fixation means comprising a compressible seal having a central lumen aligned with the axial lumen and configured for snugly receiving the lead therethrough, and compressing means for holding the seal under compression, whereby the seal central lumen is compressed to fixedly engage the lead.

22. The system as described in claim 21, wherein the baseplate means comprises at least one slot extending radially from the axial lumen, and further comprising connection means for providing a 90 degree path from the axial lumen into the slot, whereby after the lead has been fixed by the fixation means it can be positioned through the slot so as to exit the baseplate at about 90 degrees relative to the baseplate lumen.

23. The system as described in claim 21, wherein the compression seal is made of silicone rubber.

24. The system as described in claim 21, further comprising right angle guide means for guiding the lead at a right angle to the axial lumen, and securing means for securing the guide means to the baseplate means.

25. The system as described in claim 21, wherein the lead is terminated just above the fixation means, and comprising connector means for electrically and mechanically connecting an extender lead to the lead just above the fixation means.

26. The system as described in claim 25, wherein the baseplate means upper portion has a pathway for receiving the connector means.

27. The system as described in claim 21, wherein the compression means has outward restraining means for restraining radially outward extension of the compressible seal, whereby when the seal is compressed it extends radially inward and engages the member.

28. A system for delivering therapy to a patient's brain comprising:

a device to emit a medical therapy;

a member having a first end and a second end, the first end coupled to the device, the second end coupled to a patient's brain, the member transmitting the emmitted medical therapy from the device to the patient's brain means for anchoring the member to a skull of a patient, the means for anchoring having baseplate means for securing to the skull, the baseplate means having an axial lumen extending therethrough configured to receive the member;

means for fixing the member to the baseplate means, the means for fixing positioned within baseplate means, the means for fixing comprising a compressible seal having a central lumen aligned with the axial lumen and configured for snugly receiving the member therethrough, and compressing means for holding the seal under compression, whereby the seal central lumen is compressed to fixedly engage the member.

29. The system as described in claim 28, wherein the member is a medical electrical lead and the device is an implantable pulse generator.

30. The system as described in claim 28, wherein the member is a catheter and the device is an implantable drug administration system.

* * * * *